United States Patent
Green

(10) Patent No.: US 6,428,560 B2
(45) Date of Patent: Aug. 6, 2002

(54) APPARATUS FOR SAFELY REMOVING A NEEDLE FROM A SUBCUTANEOUS SEPTUM

(76) Inventor: Christopher H. Green, 2101 Atlantic Shores Blvd., Hallandale, FL (US) 33009

(*) Notice: Subject to any disclaimer, the term of this patent is extended or adjusted under 35 U.S.C. 154(b) by 0 days.

(21) Appl. No.: 09/789,166

(22) Filed: Feb. 19, 2001

Related U.S. Application Data
(60) Provisional application No. 60/194,762, filed on Mar. 31, 2000.

(51) Int. Cl.$^7$ ................................................ A61B 17/28
(52) U.S. Cl. ...................................... 606/207; 606/147
(58) Field of Search .................... 606/205–211, 174, 606/151, 157–159, 119–122

(56) References Cited

U.S. PATENT DOCUMENTS

| | | |
|---|---|---|
| 4,755,170 A | 7/1988 | Golden |
| 4,938,514 A | 7/1990 | D'Addezio |
| 5,061,248 A | 10/1991 | Sacco |
| 5,143,414 A | 9/1992 | Rosellini |
| 5,156,426 A | 10/1992 | Graves |
| 5,219,354 A * | 6/1993 | Choudhury et al. ........ 606/174 |
| 5,336,193 A | 8/1994 | Rom et al. |
| 5,460,612 A | 10/1995 | Madore |
| 5,476,452 A | 12/1995 | Thompson |
| 5,571,092 A | 11/1996 | Thompson |
| 5,637,099 A | 6/1997 | Durdin et al. |
| 5,693,069 A * | 12/1997 | Shallman .................... 606/207 |
| 5,709,660 A | 1/1998 | Doyle et al. |
| 5,911,707 A | 6/1999 | Wolvek et al. |
| 6,051,004 A * | 4/2000 | Gill ............................ 606/207 |

* cited by examiner

*Primary Examiner*—Kevin T. Truong
(74) *Attorney, Agent, or Firm*—Clifford W. Browning; Woodard, Emhardt, Naughton, Moriarty & McNett

(57) ABSTRACT

An apparatus for safely removing a needle from a subcutaneous septum, comprising a pair of blades, each having corresponding first and second ends, pivotally jointed together at their first ends whereby the blades are pivotal between a closed position in which the blades are substantially overlapped and an open position in which the second ends of the blades are spaced apart; and a concave groove in an edge of each blade at the second ends thereof positioned such that each groove is directly opposite the other in a mirrored relationship when the blades are in the open position.

2 Claims, 3 Drawing Sheets

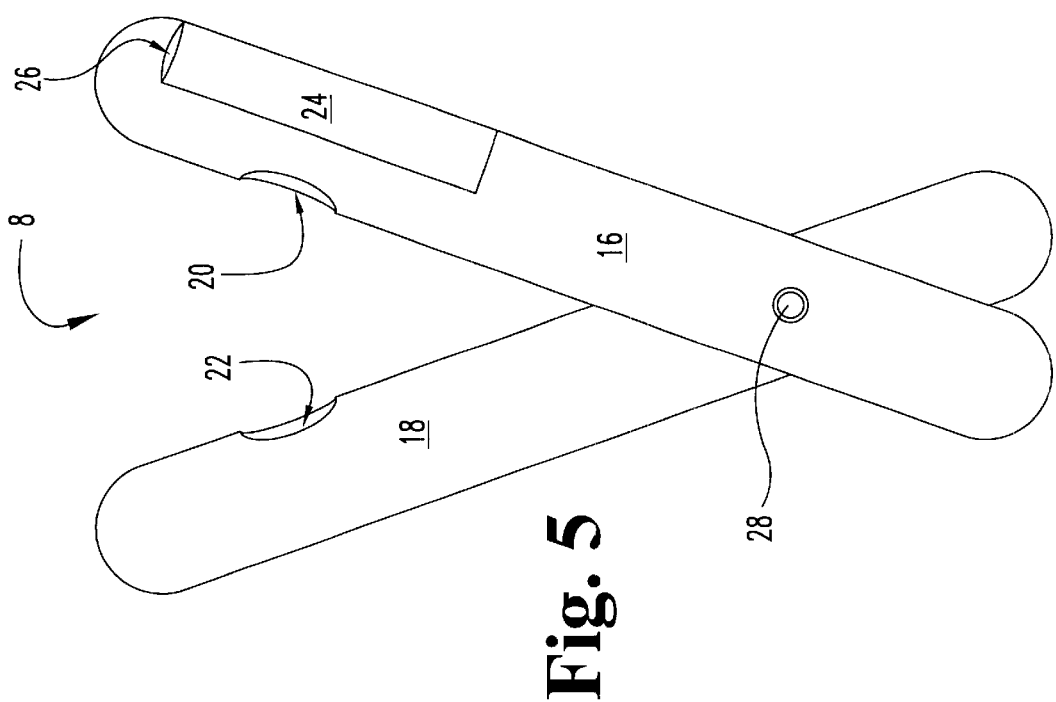
Fig. 5
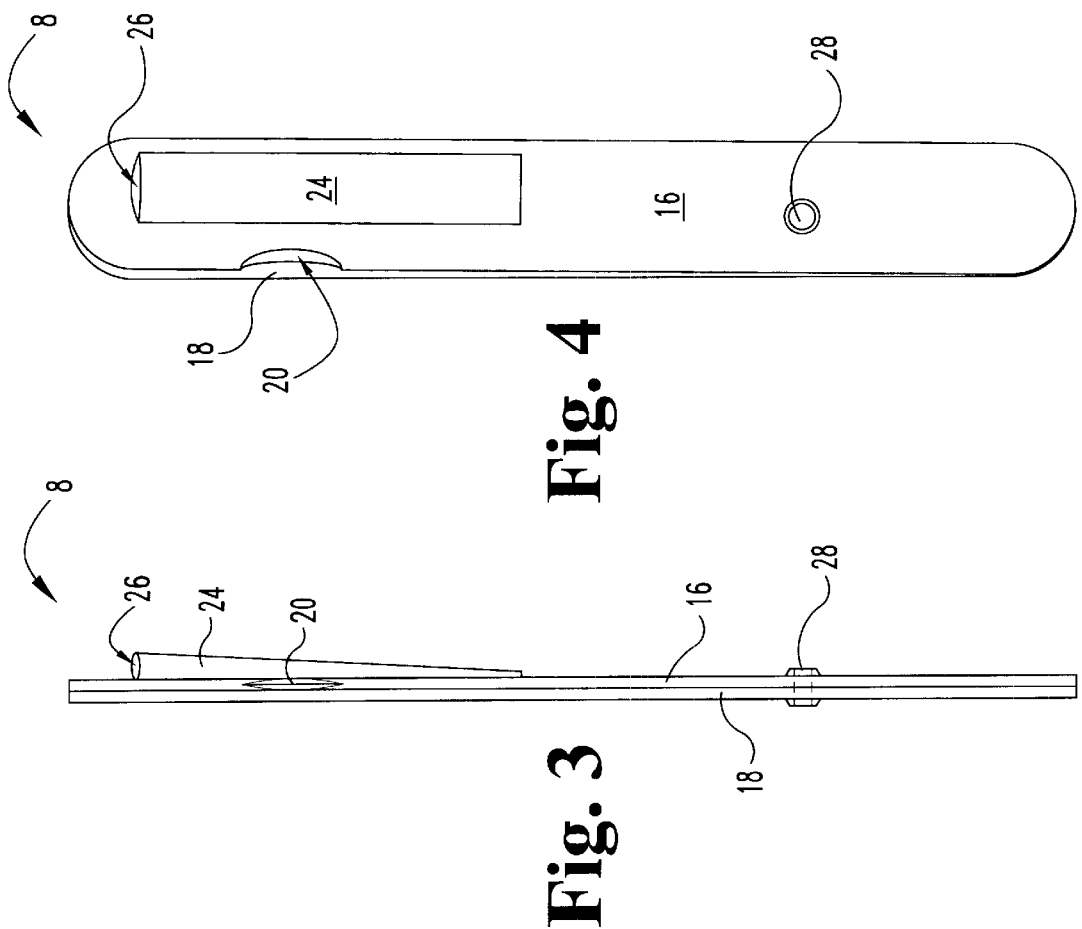
Fig. 4
Fig. 3

APPARATUS FOR SAFELY REMOVING A NEEDLE FROM A SUBCUTANEOUS SEPTUM

This application claims the benefit of prior, copending provisional patent application Ser. No. 60/194,762, filed Mar. 31, 2000.

BACKGROUND OF THE INVENTION

The present invention relates generally to devices used with implantable vascular access ports having a subcutaneous septum, and more particularly, to a novel apparatus for safely removing a needle from such subcutaneous septum without the risk of accidental needle/hand contact.

Care givers time after time come in contact with an implantable vascular access device 10, also referred to as a port, or portal (FIG. 1). In the center of the portal 10 is a self-sealing silicone septum 12. This device is surgically implanted under the skin and below the collarbone, as illustrated in FIG. 1. To access the portal, a Huber needle 14, or the like, is placed through a patient's skin with enough pressure to penetrate the silicone septum 12.

Problems start when care givers are removing the needle 14 from the septum 12 of portal 10. Extreme caution is needed because one must typically place the fingers of one hand firmly over the portal 10, which is located under the skin, to apply a counter pressure to the portal 10 as a needle is being removed from the portal 10 with the care giver's other hand. Just the right amount of counter pressure is needed on the portal 10 to permit safe removal of the needle 14, but this procedure places the care giver's fingers within millimeters of the needle 14. The principal fear is that when pulling the needle 14 out of this portal 10 with one hand, the counter pressure applied with the other hand causes a "bounce back" phenomenon when the needle is dislodged and withdrawn, making a contaminated needle stick of the care giver's hand or the patient possible.

SUMMARY OF THE INVENTION

The solution to this problem is to use as a safety device the apparatus of the present invention, which allows a care giver's fingers that apply counter pressure to the subcutaneous portal 10 to be kept at a safe distance from the contaminated needle being withdrawn. The solution is illustrated and demonstrated in FIGS. 1–5. By placing sterile wood or plastic extension pieces 16, 18 upon the patient's chest wall over the portal 10, the same amount of counter pressure applied by a care giver's fingers is now transferred to the portal 10 by the sterile extension pieces 16, 18, also referred to as blades, thus keeping the care giver's fingers out of harms way. FIGS. 1 and 2 show in detail the relationship between the apparatus 8 of the present invention and a subcutaneous portal 10 within a patient's body.

BRIEF DESCRIPTION OF THE DRAWING FIGURES

FIG. 3 is left side view of the apparatus of FIG. 1 in a storage position.

FIG. 4 is a top view of the apparatus of FIG. 3.

FIG. 5 is a top view of the apparatus of FIG. 3 in an open position.

DETAILED DESCRIPTION OF THE PREFERRED EMBODIMENT

Figure 1:
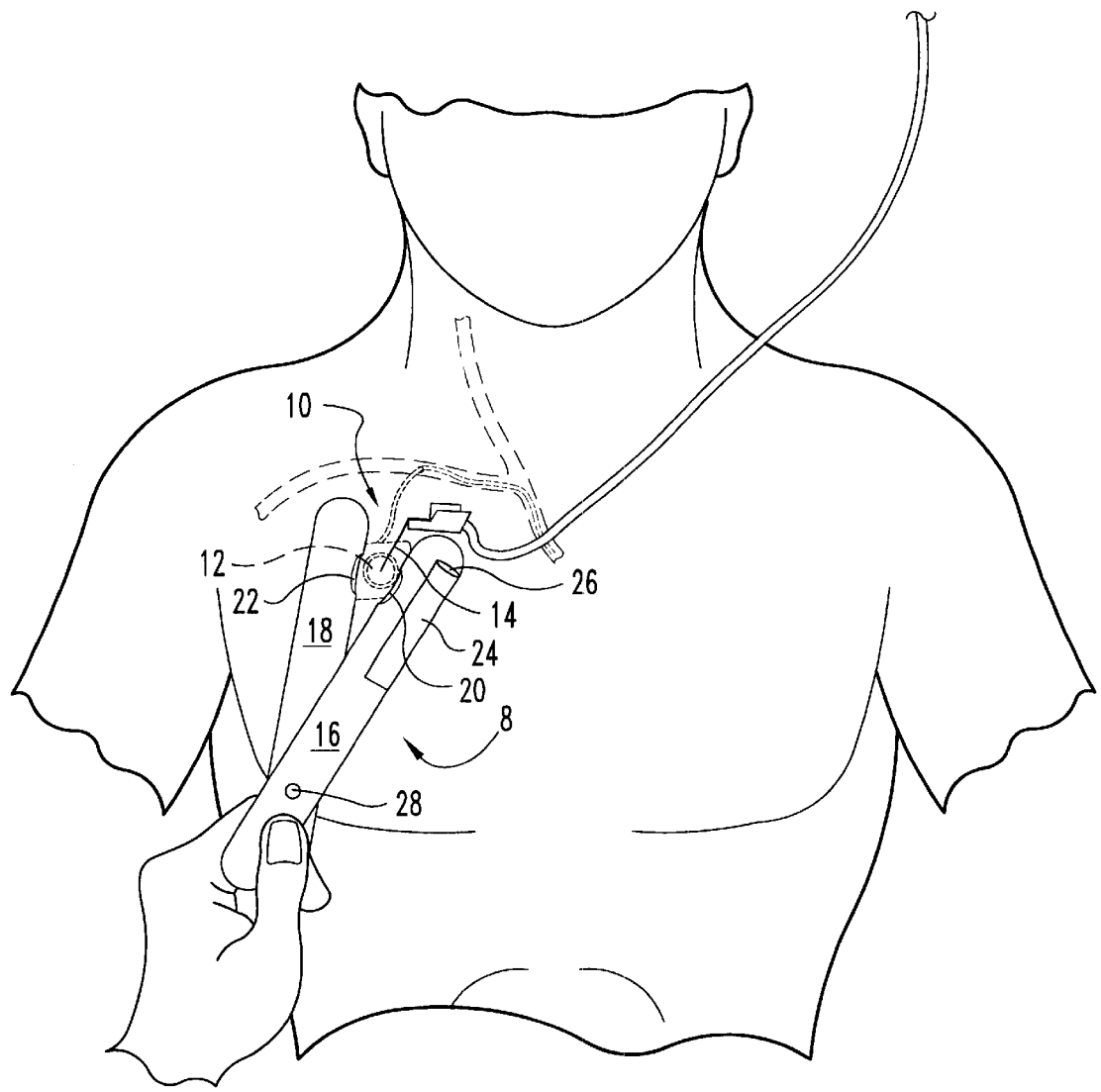
FIG. 1 is a top view of the apparatus for safely removing a needle from a subcutaneous septum of the present invention shown in an open position and in place over a subcutaneous septum.

To implement the apparatus 8 of the present invention, the two extension pieces 16, 18, also referred to as blades, shown in FIGS. 3–5 may be made of wood, plastic or any material shown to have similar properties and that may be sterilized. The blades 16, 18 of the preferred embodiment to date are approximately 1.5 cm in length, 2 mm in height and 2 cm in width.

Approximately 2.6 cm from the distal tip of each blade 16, 18 (FIGS. 3–5) is a concave groove 20, 22 approximately 1.5 cm in length and 3 mm at its center point in the preferred embodiment to date (FIG. 5). Concave grooves 20, 22 are constructed bilaterally on each blade 16, 18, as best illustrated in FIG. 5.

Bound to blade 20 by an epoxy or other stable mechanism, or if blade 20 is made of plastic, injection molded as one piece with blade 20, is a needle shield casing 24, which in the preferred embodiment to date is approximately 5.8 cm in length, 1.3 cm in width and approximately 4mm in height at its open distal tip 26, decreasing in height so as to close to approximately zero at the 5.8 cm mark. This casing 24 will be filled with a Styrofoam filling, or a material that resembles such a substance, that will enable casing 24 to tightly grip and thus retain a needle entering the casing 24.

Figure 2:
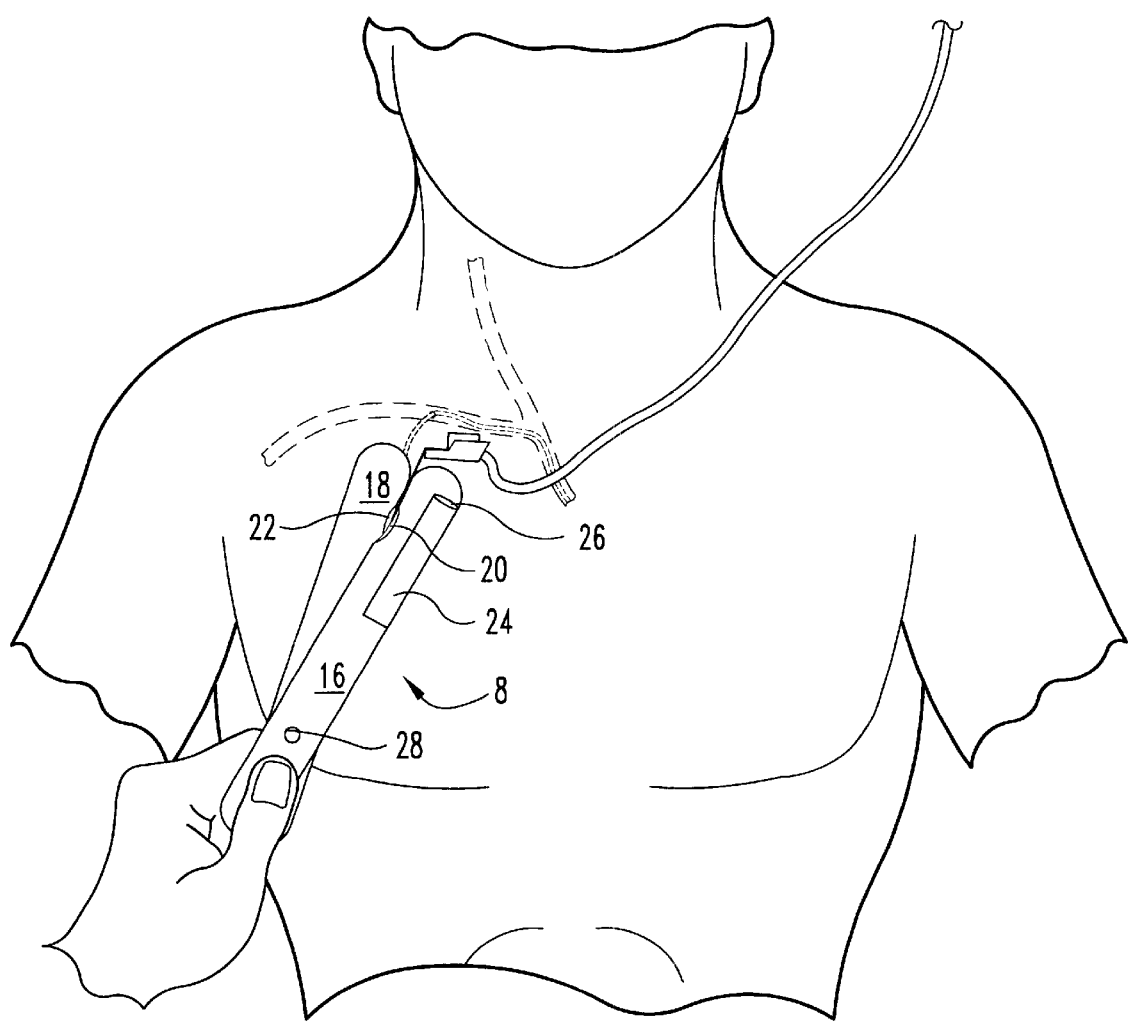
FIG. 2 is a top view of apparatus of FIG. 1 shown in a closed position in place over a subcutaneous septum.

To construct the present invention, place both blades 16, 18 on top of each other (FIG. 4). Puncture through the two blades 16, 18 with a circular metal divot 28, or alternatively, place an elastic band over both blades 16, 18 approximately 4.2 cm up the blades 16, 18. Spread open blades 16, 18 to resemble an "X" shape (FIG. 5). Place the end of the blades 16, 18 with the concave grooves 20, 22 at the left and right side of the subcutaneous septum 12 (FIG. 1). Then close the blades 16, 18 so that they gently touch a needle 14 to be removed from the septum 12 (FIG. 2). A care giver would then place a thumb upon the circular metal divot 28, or alternatively the elastic band. Applying firm pressure to the divot 28 with one hand, the care giver would use the other hand to remove needle 14. The care giver would immediately place the needle 14 into the open end 26 of the needle shield casing 24. This will then allow for a safe transfer of the needle 14, with the apparatus 8, to a Sharps container, thereby eliminating the threat of an accidental needle re-puncture of the care giver, or patient.

I claim:

1. An apparatus for safely removing a needle from a subcutaneous septum, consisting of:
   a pair of blades, each having corresponding first and second ends, pivotally jointed together at their first ends whereby the blades are pivotal between a closed position in which the blades are substantially overlapped, one on top of the other, and an open position in which the second ends of the blades are spaced apart; and
   a concave groove in an edge of each blade at the second ends thereof positioned such that each groove is directly opposite the other in a mirrored relationship when the blades are in the open position.

2. The apparatus of claim 1, and further comprising
   a needle shield casing at the second end of one of the blades.

* * * * *